US010314778B2

(12) United States Patent
Malle et al.

(10) Patent No.: US 10,314,778 B2
(45) Date of Patent: *Jun. 11, 2019

(54) ANHYDROUS OIL BASED ON PARTICLES ENCAPSULATING A BENEFICIAL AGENT

(71) Applicant: L'OREAL, Paris (FR)

(72) Inventors: Gérard Malle, Villiers S/Morin (FR); Tiina Luukas, Sevran (FR); Isabelle Bara, La Verenne St Hilaire (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/324,132

(22) PCT Filed: Jul. 1, 2015

(86) PCT No.: PCT/EP2015/065008
§ 371 (c)(1),
(2) Date: Jan. 5, 2017

(87) PCT Pub. No.: WO2016/005249
PCT Pub. Date: Jan. 14, 2016

(65) Prior Publication Data
US 2017/0209361 A1   Jul. 27, 2017

(30) Foreign Application Priority Data
Jul. 9, 2014   (FR) .................................... 14 56633

(51) Int. Cl.
| *A61K 8/92*  | (2006.01) |
| *A61K 8/60*  | (2006.01) |
| *A61K 8/73*  | (2006.01) |
| *A61K 8/11*  | (2006.01) |
| *A61Q 15/00* | (2006.01) |
| *A61Q 13/00* | (2006.01) |

(52) U.S. Cl.
CPC .................. *A61K 8/92* (2013.01); *A61K 8/11* (2013.01); *A61K 8/60* (2013.01); *A61K 8/732* (2013.01); *A61K 8/738* (2013.01); *A61Q 13/00* (2013.01); *A61Q 15/00* (2013.01); *A61K 2800/31* (2013.01); *A61K 2800/412* (2013.01)

(58) Field of Classification Search
None
See application file for complete search history.

(56) References Cited

U.S. PATENT DOCUMENTS

| 3,971,852 | A  |   | 7/1976 | Brenner et al. |           |
|-----------|----|---|--------|----------------|-----------|
| 5,506,353 | A  |   | 4/1996 | Subramaniam    |           |
| 5,508,259 | A  |   | 4/1996 | Holzner et al. |           |
| 6,200,949 | B1 | * | 3/2001 | Reijmer ........ | C11D 3/001 |
|           |    |   |        |                | 510/334   |
| 2004/0029750 | A1 |   | 2/2004 | Schudel et al. |           |
| 2008/0213380 | A1 |   | 9/2008 | Woeriee et al. |           |

FOREIGN PATENT DOCUMENTS

| DE | 10-2008-035013 A1 |   | 1/2010 |
| JP | 2008-156236 A     |   | 7/2008 |
| JP | 2008156236 A      | * | 7/2008 |

OTHER PUBLICATIONS

Machine translation into English of JP 2008-156236 A.*
Helena C.F. Carneiro, Renata V. Tonon, Carlos R.F. Grosso, Miriam D. Hubinger. Encapsulation efficiency and oxidative stability of flaxseed oil microencapsulated by spray drying using different combinations of wall materials. Journal of Food Engineering 115 (2013) 443-451. (Year: 2013).*
Martin et al., "Encapsulation and Co-Precipitation Process with Supercritical Fluids: Application with Essential Oils", The Open Chemical Engineering Journal, 2010, 4, 31-41.
Wikipedia, "Kelvin," last edited Dec. 21, 2017; https://en.wikipedia.org/wiki/Kelvin.
Wikipedia, "Maltodextrin," last edited Jan. 10, 2018; https://en.wikipedia.org/wiki/Maltodextrin.
Horiba, "Particle size result interpretation: number vs. volume distributions," printed 2018; http://www.horiba.com/scientific/products/particle-characterization/education/general-information/data-interpretation/number-vs-volume-distributions/.
MSDS "Peppermint oil," Jun. 4, 2015; http://www.thegoodscentscompany.com/msds/md100305.html.
Silva et al., "Influence of different combinations of wall materials and homogenization pressure on the microencapsulation of green coffee oil by spray drying," Food Research International 61:132-143, 2014, available online Jan. 30, 2014.
Garcia et al., "Effect of Homogenization Pressure and Oil Load on the Emulsion Properties and the Oil Retention of Microencapsulated Basil Oil (*Ocimum basilicum* L.)" Drying Technology 30:1413-1421, 2012.

* cited by examiner

*Primary Examiner* — Michael P Cohen
(74) *Attorney, Agent, or Firm* — Polsinelli PC

(57) ABSTRACT

The present invention relates to an anhydrous composition comprising:
1) at least particles comprising a core containing at least one beneficial agent and an envelope surrounding the core; said envelope comprising at least one hydrophobically modified polysaccharide and at least one water-soluble carbohydrate and/or water-soluble polyol;
said particles simultaneously having a poured powder density ranging from 300.0 g/l to 600.0 g/l and an absolute density of greater than 1.0; and
2) an oily phase.
The invention additionally relates to a cosmetic process for caring for and/or for making up a keratin material, which consists in applying to the surface of said human keratin material a consumer product comprising a composition as defined previously.
The present invention also relates to a cosmetic process for treating body odor and optionally human perspiration, which consists in applying to the surface of the keratin material a composition as defined previously comprising at least one deodorant active agent and/or antiperspirant active agent.

17 Claims, No Drawings

ANHYDROUS OIL BASED ON PARTICLES ENCAPSULATING A BENEFICIAL AGENT

CROSS REFERENCE TO RELATED APPLICATIONS

This application is a National Phase filing under 35 U.S.C. § 371 of PCT/EP2015/065008 filed on Jul. 1, 2015; and this application claims priority to Application No. 1456633 filed in France on Jul. 9, 2014 under 35 U.S.C. § 119. The entire contents of each application are hereby incorporated by reference.

The present invention relates to an anhydrous composition in oil form comprising:
1) at least particles comprising a core containing at least one beneficial agent and an envelope surrounding the core; said envelope comprising at least one hydrophobically modified polysaccharide and at least one water-soluble carbohydrate and/or water-soluble polyol;
said particles simultaneously having a poured powder density ranging from 300.0 g/l to 600.0 g/l and an absolute density of greater than 1.0; and
2) an oily phase.

The invention additionally relates to a cosmetic process for caring for and/or for making up a keratin material, which consists in applying to the surface of said human keratin material a consumer product comprising a composition as defined previously.

The present invention also relates to a cosmetic process for treating body odor and optionally human perspiration, which consists in applying to the surface of the keratin material a composition as defined previously comprising at least one deodorant active agent and/or antiperspirant active agent.

Many cosmetic presentation forms allow the dispensing of beneficial agents especially in the cosmetic industry, in the pharmaceutical industry, in perfumery; in products intended for veterinary use, especially hygiene products and/or animal care products; in household maintenance products such as laundry care and/or cleaning products; in maintenance products for domestic electrical appliances; in maintenance products for floors, tiles, wood, etc.; in sanitary products; in textile maintenance products; in maintenance products for leather goods such as shoes and soles; in products derived from the agrifood industry; in agricultural products; in plant protection products; in paints; in inks; in maintenance products in the motor vehicle industry.

Among these, compositions in oil form constitute a category of products that are appreciated by consumers for their ease of spreading and of application, especially in cosmetics. They are used in particular in the field of antisun products, but may also be profitably exploited in products for making up or caring for keratin materials such as the skin, such as bodycare oils such as massage oils, or for the face or the lips, self-tanning oils or oils for caring for and/or conditioning and/or styling the hair such as hairstyling oils.

The aim of the present invention is to propose novel cosmetic compositions of anhydrous oil type comprising at least one beneficial agent encapsulated in particles that are leaktight in the absence of moisture, i.e. odorless if the active agent is a perfume said particles having a low poured powder density to facilitate their formulation and keep a light and soft texture said particles also needing to be compatible with the usual ingredients of these formulations and strong enough to be able to be formulated as an oily dispersion without being damaged said beneficial agent contained in the particles being able to be released virtually immediately, gradually and repeatably on the skin, the hair and the integuments on contact with water.

It is known that there is a need in many industrial fields to protect a certain number of fragile or volatile molecules and to control their release into an external medium.

One of the means for achieving such an aim is to encapsulate them. The object of this encapsulation is to reduce the evaporation and the transfer of the active material toward the environment, either during storage or during the production of the products, or alternatively during their use. Said encapsulation may also make the material easier to use by diluting it and by promoting its uniform distribution in the support.

Microencapsulation includes all the technologies for coating or trapping active principles in solid, liquid or gaseous form inside individualized particles whose size ranges between a few microns and a few millimeters. If these microparticles are hollow (vesicular), they are referred to as microcapsules, and if they are filled (matrix-based), they are referred to as microspheres. Their size ranges from 1 µm to more than 1000 µm. These microparticles may or may not be biodegradable and may contain between 5% and 90% (by mass) of active substance.

The encapsulated active substances are of very varied origin: pharmaceutical or cosmetic active principles, food additives, plant protection products, fragranced essences, microorganisms, cells, or alternatively chemical reaction catalysts, etc.

The entire advantage of encapsulation microparticles lies in the presence of a polymer membrane, which isolates and protects the contents from the external medium. Depending on the case, the membrane will be destroyed during use to release its contents (for example: "scratch and sniff" advertising inserts which release perfume when the microcapsules are crushed), or alternatively the membrane will remain present throughout the release of the contents, the rate of diffusion of which it will control (for example: encapsulation of medicaments for sustained release).

The coating materials are generally hydrophobic or hydrophilic polymers of natural or synthetic origin, or alternatively lipids.

The main processes for performing the encapsulation of substances in microparticles are interfacial polymerization, interfacial crosslinking, emulsification followed by evaporation or extraction of the solvent, double emulsification evaporation/extraction of solvent, spray-drying, prilling and coacervation.

U.S. Pat. No. 5,508,259 proposes nonaqueous fragrancing compositions, comprising perfumes encapsulated in water-soluble particles. Said capsules are obtained via conventional encapsulation techniques and in particular the spray-drying of an emulsion formed from a film-forming solid substrate in combination with an emulsifying agent and a mixture of fragrancing ingredients. The film-forming solid substrate is especially chosen from polyvinyl acetate, polyvinyl alcohol, dextrins, natural or modified starch, plant gums, pectins, xanthans, alginates, carrageenans or alternatively cellulose derivatives, for instance carboxymethylcellulose, methylcellulose or hydroxyethylcellulose. The emulsion is then dehydrated via a standard atomization (spray-drying) process, which consists, as described in Example 1, in spraying it as fine droplets in an atomizer at a flow rate of 50 kg/h and a pressure of 0.45 bar, in contact with an air stream at 320 m³/h heated to 350° C. so as to evaporate the water, which makes it possible to obtain a fine powder with a particle diameter of between 20 and 80 microns and containing 20% by weight of perfume.

However, it was noted that the particles obtained via this process were highly odorous in dry form on account of the presence of free (non-encapsulated) perfume, that they were formed mainly from agglomerates that were liable to harm the homogeneity of the product and prevent correct application of the product, and that they did not have the density characteristics suitable for the objective of the invention.

U.S. Pat. No. 6,200,949 also describes a process for forming a particulate material containing a hydrophilic perfume, comprising the successive steps consisting in forming an aqueous emulsion of perfume containing 40% to 60% by weight of water, 3% to 30% by weight of maltodextrin and 10% to 40% by weight of hydrophobically modified starch, and then in drying it by spraying in an atomizer (air stream of 420 m³/h heated to 204° C.) so that the particles are formed with a mean size of from about 3 to about 10 microns and a perfume content of from 15% to 50% by weight.

However, the particles obtained via this process are highly odorous in dry form on account of the presence of free (non-encapsulated) perfume, they are formed mainly from agglomerates, are liable to harm the homogeneity of the product and do not have the density characteristics suitable for the objective of the invention.

It is clearly very important to be able to provide leaktight particles which release their contents only on demand (in response to the ambient moisture, especially in humid climatic zones, in response to body perspiration, shampooing or showering, etc.), firstly to ensure protection over time of the encapsulated active agent, above all if it is fragile and/or volatile, and secondly to avoid interactions with the other ingredients of the formulation. When the encapsulated beneficial agent is a fragrancing ingredient and/or a whole perfume, it is all the more important for the encapsulation to be total, which leads to odorless particles in anhydrous formulations allowing the formulator to combine them, if desired, with any free perfume of his choice (identical or different) without any risk of interactions or of disruption of the chosen fragranced note.

Patent EP 1 917 098 B1 proposes a process for preparing encapsulation products by precipitation, said process using:
 a pumpable emulsion comprising (i) a continuous phase containing a solvent and a solute forming a matrix dissolved in said solvent and (ii) a dispersed phase;
 an extractor comprising a supercritical, subcritical or liquefied gas;
said solvent being substantially more soluble in the extractor than said solute forming a matrix, and said process comprising the successive steps consisting in:
a. combining the pumpable emulsion with the extractor under mixing conditions;
b. allowing the formation of particulate encapsulation products in which the dispersed phase is embedded in a solid matrix of the solute forming a matrix;
c. collecting the encapsulation products and separating them from the extractor.

It is indicated that this process may be used in the pharmaceutical and agrifood industries and also in the fields of agriculture, coating, adhesives and catalysts. It may be used in particular for encapsulating pharmaceutical active agents, flavorings, enzymes, dyes, pesticides and herbicides.

After extensive research, the Applicant has discovered, surprisingly and unexpectedly, that it is possible to achieve the objectives as stated previously by using, in an anhydrous composition in oil form comprising at least one oily phase and particles releasing a beneficial agent comprising a core containing at least one beneficial agent and an envelope surrounding the core; said envelope comprising at least one hydrophobically modified polysaccharide and at least one water-soluble carbohydrate and/or water-soluble polyol; said particles simultaneously having a poured powder density ranging from 300.0 g/l to 600.0 g/l and an absolute density of greater than 1.0. These particles may be obtained in particular via the process as described in patent EP 1 917 098 B1 commented previously.

The particles releasing a beneficial agent in accordance with the present invention make it possible to encapsulate beneficial ingredients, which are in particular fragile, completely (total encapsulation), without degradation, in capsules that are strong enough and leaktight enough to be able to be stored without impairment in the absence of moisture, and which can be readily formulated and remain stable in anhydrous compositions in oil form. These same particles of this type of composition preferably have spherical morphology and a very low poured powder density to conserve the light and soft texture; they also have the capacity of opening in the presence of water to be able to release their beneficial agent virtually immediately, gradually and repeatably on the skin, the hair and the integuments on contact with water. This discovery forms the basis of the present invention.

The present invention relates to an anhydrous composition in oil form comprising:
1) at least particles comprising a core containing at least one beneficial agent and an envelope surrounding the core; said envelope comprising at least one hydrophobically modified polysaccharide and at least one water-soluble carbohydrate and/or water-soluble polyol;
said particles simultaneously having a poured powder density ranging from 300.0 g/l to 600.0 g/l and an absolute density of greater than 1.0; and
2) an oily phase.

The invention additionally relates to a cosmetic process for caring for and/or for making up a keratin material, which consists in applying to the surface of said human keratin material a consumer product comprising a composition as defined previously.

The present invention also relates to a cosmetic process for treating body odor and optionally human perspiration, which consists in applying to the surface of the keratin material a composition as defined previously comprising at least one deodorant active agent and/or antiperspirant active agent.

Preferably, the composition comprises a physiologically acceptable medium and, more preferentially, cosmetically acceptable.

The compositions in anhydrous oil form according to the invention may also be used in other fields such as products for veterinary use, especially hygiene products and/or animal care products; household maintenance products such as laundry care and/or cleaning products; maintenance products for domestic electrical appliances; maintenance products for floors, tiles, wood, etc.; sanitary products; textile maintenance products; maintenance products for leather goods such as shoes and soles; products derived from the agrifood industry; agricultural products; plant protection products; paints; inks; maintenance products in the motor vehicle industry.

Definitions

For the purposes of the present invention, the term "anhydrous composition" means a composition with a water content of less than 5% by weight, preferably less than 2% by weight and even more preferably less than 1% by weight relative to the weight of said composition, or alternatively even less than 0.5% and especially free of water. In this definition, the water mentioned includes the residual water provided by the mixed ingredients.

The term "composition in oil form" means a composition that is liquid at 25° C. and atmospheric pressure (760 mmHg) formed essentially from an oily phase.

For the purposes of the present patent application, the term "oily phase" means an oily phase that is liquid at room temperature (25° C.) and atmospheric pressure (760 mmHg), composed of one or more mutually compatible fatty substances that are liquid at room temperature, also known as oils.

For the purposes of the present invention, the term "physiologically acceptable medium" is intended to denote a medium that is suitable for the topical administration of a composition. A physiologically acceptable medium is a medium which has no odor and/or unpleasant appearance, and which is perfectly compatible with topical administration.

The term "keratin material" means the skin, the scalp, the lips and/or integuments such as the nails and keratin fibers, for instance bodily hair, the eyelashes, the eyebrows and head hair.

For the purposes of the invention, the term "cosmetic composition" means any composition applied to the surface of a keratin material to produce a non-therapeutic hygiene, care, conditioning or makeup effect contributing toward improving the well-being and/or enhancing the beauty and/or modifying the appearance of the keratin material onto which said composition is applied.

For the purposes of the invention, the term "dermatological composition" means any composition applied to the surface of a keratin material to prevent and/or treat a disorder or dysfunction of said keratin material.

For the purposes of the invention, the term "cosmetic treatment" means any non-therapeutic fragrancing, hygiene, care, conditioning or makeup effect contributing toward improving the well-being and/or enhancing the beauty and/or modifying the appearance or odor of the keratin material onto which said composition is applied.

The term "consumer product" means any manufactured product intended to be used or consumed in the form in which it is sold and which is not intended for a subsequent manufacture or modification. Without the examples being limiting, the consumer products according to the invention may be cosmetic products also including cosmetic formulations for caring for and/or for the hygiene of the skin, the lips, or the hair; dermatological products; fragrancing products; pharmaceutical products; products for veterinary use, especially animal hygiene and/or care products; household maintenance products such as laundry care and/or cleaning products; products for maintaining domestic electrical appliances; products for maintaining floors, tiles, wood, etc.; sanitary products; textile maintenance products; maintenance products in leather goods such as shoes and soles; products derived from the agrifood industry; agricultural products; plant protection products; paints; inks; maintenance products in the motor vehicle industry.

For the purposes of the invention, the term "beneficial agent" means any compound present in a consumer product which produces a beneficial effect perceived by the consumer during its use and/or obtained on the consumer product itself, said beneficial effect possibly being a sensory improvement or a modification, which is especially visual and/or olfactory and/or tactile, an improvement in the comfort and/or ease of application, an esthetic effect, a hygiene effect, a sensation of cleanliness, or a curative and/or prophylactic effect.

The term "particles comprising a core containing at least one beneficial agent" means a particle comprising at least one beneficial agent which is immobilized, captured and/or encapsulated in the matrix of an encapsulation or trapping system; said beneficial agent being released to the exterior gradually as the encapsulation or trapping system deteriorates when its degradation takes place on contact with a medium with which it reacts or under the effect of a stimulus such as a supply of water.

Poured Powder Density (or Loose Bulk Density)

The determination is performed at room temperature (20-25° C.) and under normal atmospheric conditions (1 atmosphere) using a 100 ml measuring cylinder. The measuring cylinder is weighed empty and then filled with a volume of 100 ml of poured powder, without tapping. The difference in mass between the empty measuring cylinder and the cylinder filled with 100 ml of powder gives the poured powder density.

Absolute Density

Measurement Principle

The measurement consists in determining the weight of a sample of the solid powder by simple weighing, followed by measuring the volume occupied by the powder particles by measuring the volume of liquid displaced by the powder sample by immersion in this liquid. The liquid chosen must be sparingly volatile and must not be a solvent for the powder. Cyclohexane is generally chosen. The measurements are performed at least twice.

Materials:

A 10 or 25 ml graduated flask and a precision balance.

$m_1$ is the weight of the empty flask.

$m_2$ is the weight of the flask filled with water up to the graduation mark.

$m_3$ is the weight of the flask filled with cyclohexane up to the graduation mark.

$m_4$ is the weight of the flask filled to about one third of its volume with the powder to be analyzed.

The flask is filled to about one third of its volume with the powder to be analyzed.

Method

The flask is filled to slightly below the graduation mark with cyclohexane. In order to completely remove the air trapped in the powder, the following are performed:

1) the flask is treated in an ultrasonic bath for 5 minutes
2) the level of cyclohexane is adjusted to the graduation mark
3) the flask is treated in an ultrasonic bath for 2 minutes
4) steps 2 and 3 are repeated if necessary, until the level of the cyclohexane no longer changes.

$m_5$ is the weight of the flask thus filled.

The weight of powder analyzed is equal to $m_4-m_1$ (for good accuracy, this weight must be greater than 2 g). Since the density of air is very low relative to that of the solid, it is taken that $m_4-m_1$ is equal.

The weight of cyclohexane corresponding to the volume occupied by the solid (Vs) is equal to:

$$m_6 = (m_3-m_1)-(m_5-m_4) = \rho_{cyclo}/Vs$$

where $\rho_{cyclo}$ is the density of cyclohexane at the temperature of the laboratory.

The absolute density of the constituent solid of the powder is equal to $\rho_{cyclo}=(m_4-m_1)/Vs=\rho_{cyclo}(m_4-m_1)/m_6$.

If the density of cyclohexane at the temperature of the laboratory is unknown, it is determined as follows relative to that of water:

If Vf is the graduated volume of the flask and $\rho_{water}$ is the density of water at the temperature of the laboratory, then:

$$\rho_{cyclo}=(m_3-m_1)/Vf \text{ and } \rho_{water}=(m_2-m_1)/Vf$$

i.e. $\rho_{cyclo}=\rho_{water}(m_2-m_1)/(m_3-m_1)$

The absolute density of the constituent solid of the powder is equal to:

$$\rho_s=[\rho_{water}(m_4-m_1)(m_2-m_1)]/[m_6(m_3-m_1)].$$

Encapsulation Particles

The particles in accordance with the invention comprise a core containing at least one beneficial agent and an envelope surrounding the core; said envelope comprising at least one hydrophobically modified polysaccharide and at least one water-soluble carbohydrate and/or a water-soluble polyol; said particles simultaneously having a poured powder density ranging from 300.0 g/l to 600.0 g/l and an absolute density of greater than 1.0.

The particles in accordance with the present invention are preferably spherical.

The term "spherical" means that the particle has a sphericity index, i.e. the ratio between its largest diameter and its smallest diameter, of less than 1.2. In this case, such particles are generally referred to as "capsules".

The term "mean size" of the particles means the parameters D[4,3] and D[2,3] measured via the dry route by laser scattering using a Microtrac S3500 particle size analyzer, the results being expressed in the form of the volume and number particle size distributions giving access to the mean diameter.

The spherical particles in accordance with the present invention thus preferably have a number-mean diameter ranging from 1 to 30 μm, more preferentially ranging from 2 to 15 μm and even better still from 5 to 10 μm and a volume-mean diameter ranging from 5 to 150 μm, preferably ranging from 10 to 100 μm and even better still from 20 to 80 μm.

The particles according to the invention containing the beneficial agent preferably represent from 0.1% to 60% by weight, preferably from 0.3% to 40% by weight and better still from 0.5% to 20% by weight relative to the total weight of the composition.

Hydrophobically Modified Polysaccharide

The term "hydrophobically modified polysaccharide" means any chemically or enzymatically modified polysaccharide comprising at least one hydrophobic functional group.

Polysaccharides are carbohydrate macromolecules formed by the linking of a large number of hydrophilic elementary sugars (saccharides) bonded together via O-oside bonds.

The hydrophobic functional groups of the present invention are hydrocarbon-based groups (formed essentially from carbon and hydrogen atoms) comprising at least 4 carbon atoms, preferably at least 6 and better still at least 8 carbon atoms, such as alkyl, alkenyl, aryl (i.e. phenyl) or aralkyl (i.e. benzyl) groups. The maximum number of carbon atoms in the hydrocarbon-based group is preferably 24, more preferentially 20 and even more preferentially 18. The hydrophobic hydrocarbon-based groups may be unsubstituted, for example formed from a simple long alkyl chain, or may be substituted with unreactive groups, for instance aromatic groups such as aryl (i.e. phenyl) or aralkyl (i.e. benzyl) groups or alternatively polar groups, for instance carboxyls or hydroxyls.

To graft the hydrophobic functional group(s) onto the polysaccharides, use is generally made of halogenated derivatives, epoxides, isocyanates, or carboxylic acids or derivatives thereof (esters, acid halides or anhydrides).

Among the hydrophobically modified polysaccharides according to the invention, preference is given to hydrophobically modified neutral polysaccharides such as:

celluloses and derivatives thereof, in particular hydrophobically modified methyl-, hydroxyethyl-, ethylhydroxyethyl-, hydroxypropyl-, hydroxypropylmethyl- and carboxymethyl-celluloses. The preferred hydrophobic groups are chosen from $C_8$-$C_{18}$ alkyl radicals and more particularly $C_{12}$-$C_{18}$ alkyl radicals. In particular, the hydrophobically modified neutral polysaccharides denote hydrophobically modified ethylhydroxyethylcellulose or hydroxyethylcellulose and especially those sold by Ashland under the trade name Natrosol Plus;

hydrophobically modified starches and derivatives thereof (in particular: hydroxyethyl-, hydroxypropyl- and carboxymethyl-starch) and also hydrophobically modified degraded and/or esterified starches, hydrophobically modified dextrans especially such as the phenoxy-dextrans obtained by reaction between 1,2-epoxy-3-phenoxypropane and a dextran; ($C_6$-$C_{12}$) alkyl-dextrans obtained by reaction between 1,2-epoxy-($C_6$-$C_{12}$)alkanes such as 1,2-epoxyoctane or 1,2-epoxydodecane and a dextran;

hydrophobically modified guars and hydroxyethyl-, carboxymethyl- and hydroxypropyl-guar derivatives thereof;

hydrophobically modified pullulans such as cholesteryl-pullulans;

inulins hydrophobically modified via alkyl ether, ester and carbamate functions, in particular carbamates bearing $C_4$-$C_{18}$ alkyl chains and more particularly those sold under the name Inutech® SP1.

The hydrophobically modified polysaccharide preferably represents from 20% to 90% by weight, especially from 30% to 80% by weight, better still from 40% to 70% by weight and even better still from 40% to 60% by weight relative to the total weight of the envelope of the particle.

According to a particularly preferred form of the invention, hydrophobically modified starches will be chosen from among the hydrophobically modified polysaccharides.

The botanical origin of the starch molecules may be cereals or tubers. Thus, the starches are chosen, for example, from corn starch, rice starch, cassava starch, tapioca starch, barley starch, potato starch, wheat starch, sorghum starch and pea starch.

The term "hydrophobically modified starch" means any chemically or enzymatically modified starch comprising at least one hydrophobic functional group.

The hydrophobically modified starches in accordance with the invention are preferably chosen from $C_{10}$-$C_{18}$ hydroxyethyl starch esters and starch $C_5$-$C_{20}$-alkyl or $C_5$-$C_{20}$ alkenyl succinates, more particularly $C_5$-$C_{20}$-alkenyl succinates and even better still sodium starch octenyl succinate (E1450-CAS 66829-29-6/52906-93-1/70714-61-3), in particular the product sold by National Starch under the name Capsul®.

Mention may also be made of the commercial references Capsul TA®, N-LOK®, N-LOK 1930®, HI-CAP 100®, Purity Gum 1773® and Purity Gum 2000® from National Starch, Cleargum CO® from the company Roquette and Emcap®, Emtex® and Delitex from the company Cargill.

Water-Soluble Carbohydrate or Polyol

The term "water-soluble carbohydrate" or "water-soluble polyol" refers to a carbohydrate or a polyol which, when introduced into water without pH modification at 25° C., at a mass concentration equal to 3%, makes it possible to obtain a macroscopically homogeneous and transparent solution, i.e. a solution with a minimum light transmittance value, at a wavelength equal to 500 nm, through a sample 1 cm thick, of at least 80% and preferably of at least 90%.

The term "carbohydrates" (also known as saccharides) means all simple sugars or oses and combinations thereof or osides.

Carbohydrates usually comprise:
(1) monosaccharides or oses which are of two types: aldoses comprising an aldehyde function on the first carbon and ketoses comprising a ketone function on the second carbon. They are also distinguished according to the number of carbon atoms they contain.
(2) oligosaccharides (or oligosides), which are saccharide oligomers bearing a sequence of 2 to 10 monosaccharide units linked via glycoside bonds.
(3) polyholosides (or polysaccharides or polyosides), which are saccharide polymers bearing a sequence of more than 10 monosaccharide units.

Water-Soluble Carbohydrates
(1) Saccharides or Monosaccharides

Among the saccharides or monosaccharides that may be used according to the invention, mention may be made, alone or as mixtures, of:
 tetroses containing four carbons: erythrose, threose, erythrulose;
 pentoses containing five carbons: ribose, arabinose, xylose, deoxyribose;
 hexoses containing six carbons: glucose, mannose, fucose, gulose, idose, galactose, talose, fuculose, fructose, sorbose, rhamnose;
 heptoses containing seven carbons: sedoheptulose in the D and/or L form thereof.

Among the monosaccharides, use will be made more preferentially of arabinose, xylose, fructose, glucose, mannose, rhamnose or threose and even more preferentially glucose or threose.

(2) Oligosaccharides

Among the oligosaccharides that may be used according to the invention, mention may be made of:
(i) disaccharides or diholosides or diosides composed of two saccharide molecules.

Among the disaccharides, mention may be made of: cellobiose, isomaltose, isomaltulose, lactose, lactulose, maltose, sucrose, trehalose or melibiose.
(ii) triholosides composed of three saccharide molecules, for instance: raffinose or maltotriose.
(iii) dextrins, which are mixtures of linear glucose oligosides in which the glucose units are linked via oside bonds of the $\alpha$-(1,4) or $\alpha$-(1,6) type.
(iv) glucose syrups obtained by acidic or enzymatic hydrolysis of starch, the D.E. of which is between 20 and 100.

D.E. or "dextrose equivalent" is the indicator of the degree of hydrolysis of starch. The higher the D.E., the more extensive the hydrolysis, and thus the higher the proportion of simple (short-chain) sugars.
(v) glucose-fructose syrups especially with a high content of fructose (HFCS: high-fructose corn syrup), which denote a series of corn syrups that have been subjected to enzymatic processes in order to increase their fructose content before being mixed with glucose syrup to obtain their final composition.

Among the glucose-fructose syrups, also known as isoglucose syrups, which may be used according to the invention, mention may be made of:
 HFCS 90, which contains 90% fructose and 10% glucose syrup;
 HFCS 55, which contains 55% fructose and 45% glucose syrup;
 HFCS 42, which contains 42% fructose and 58% glucose syrup.

Among the oligosaccharides, use will be made more preferentially of cellobiose, maltose, isomaltose, raffinose and glucose syrups, more particularly glucose syrups.

Use will be made preferentially of a glucose syrup with a D.E. ranging from 21 to 60 and even more preferentially a glucose syrup with a D.E. of from 21 to 38, for instance the dehydrated glucose syrups sold by Tereos under the names G210, G290 and G380.

(3) Polysaccharides or Polyholosides

Examples that may be mentioned include:
 dextrans, which are composed of D-glucose units linked via an $\alpha(1\rightarrow 6)$ oside bond and bearing branches formed from alpha-1,2 or 1,3 or 1,4 bonds. They are prepared by fermentation of beet sugar solely containing hydroxyl groups. It is possible to obtain dextran fractions of different molecular weights from native dextran by hydrolysis and purification. The dextran may in particular be in the form of dextran sulfate.
 pullulans, which are formed from maltotriose units, known under the name $\alpha(1,4)$-$\alpha(1,6)$-glucan. Three glucose units in maltotriose are connected via an $\alpha$-(1,4) glycoside bond, whereas the consecutive maltotriose units are connected to each other via an $\alpha$-(1,6) glycoside bond. It is produced from starch by the fungus *Aureobasidium pullulans*. Pullulan is produced, for example, under the reference Pullulan PF 20® by the group Hayashibara in Japan.
 maltodextrins, which are the result of hydrolysis of a cereal (i.e.: wheat, corn) starch or of a tuber (i.e.: potato) starch. They are formed from various sugars (i.e.: glucose, maltose, maltotriose, oligosaccharides and polyosides) derived directly from this reaction, in proportions which depend on the degree of hydrolysis.

This degree is measured by the "dextrose equivalent", or D.E., dextrose or D-glucose being the result of a total hydrolysis of starch. The higher the D.E., the more extensive the hydrolysis, and thus the higher the proportion of simple (short-chain) sugars of which maltodextrin is composed.

The maltodextrins used in accordance with the invention preferentially have a D.E. ranging from 4 to 20 and better still maltodextrins with a D.E. ranging from 12 to 20.

Use will preferably be made of potato or corn maltodextrins such as those sold under the trade names MD 20P® from Avebe and Maldex 120®, Maldex 170® and Maldex 190® from Tereos.

Polyols

For the purposes of the invention, polyols are linear, branched and/or cyclic, non-glycoside, saturated or unsaturated carbon-based and especially hydrocarbon-based compounds, comprising 4 to 18 carbon atoms, especially 4 to 16, or even 4 to 12 carbon atoms, and 3 to 9 hydroxyl (OH) groups, and also possibly comprising one or more oxygen atoms intercalated in the chain (ether function).

The polyols in accordance with the invention are preferably linear or branched saturated hydrocarbon-based compounds, comprising 4 to 18 carbon atoms, especially 4 to 16 or even 4 to 12 carbon atoms, and 3 to 9 hydroxyl (OH) groups.

They may be chosen, alone or as mixtures, from:
triols, such as trimethylolethane or trimethylolpropane;
tetraols such as pentaerythritol (tetramethylolmethane), erythritol, diglycerol or ditrimethylolpropane;
pentols such as arabitol;
hexols such as dulcitol, sorbitol, mannitol, dipentaerythritol or triglycerol;
heptols such as volemitol;
octaols;
nonanols such as isomalt, maltitol, isomaltitol or lactitol.

Preferably, the polyol is chosen from sorbitol, maltitol, mannitol and isomalt, and mixtures thereof.

Among the water-soluble carbohydrates and water-soluble polyols in accordance with the invention, the ones that will more particularly be chosen are water-soluble oligo- and polysaccharides and more preferentially dextrans, pullulans, glucose syrups and maltodextrins and better still glucose syrups with a D.E. ranging from 21 to 38 and/or maltodextrins with a D.E. ranging from 4 to 20 and better still maltodextrins with a D.E. ranging from 12 to 20.

Use will preferably be made of glucose syrups such as those sold by Tereos under the names G210, G290 and G380 and potato or corn maltodextrins such as those sold under the trade names MD 20P® from Avebe and Maldex 120®, Maldex 170® and Maldex 190® from Tereos.

The water-soluble carbohydrate(s) and/or polyol(s) in accordance with the invention represent from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the particles according to the invention is formed from
a) at least one starch ($C_5$-$C_{20}$)alkenyl succinate and
b) at least one maltodextrin with a D.E. ranging from 4 to 20 and preferably ranging from 12 to 20 and/or a glucose syrup with a D.E. ranging from 21 to 60 and preferentially from 21 to 38.

According to a first variant, the envelope of the particles according to the invention is formed from at least one starch ($C_5$-$C_{20}$)alkenyl succinate and from at least one maltodextrin with a D.E. ranging from 4 to 20 and preferably ranging from 12 to 20.

According to a second variant, the envelope of the particles according to the invention is formed from at least one starch ($C_5$-$C_{20}$)alkenyl succinate and from at least one glucose syrup with a D.E. ranging from 21 to 60 and preferentially ranging from 21 to 38.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and
b) at least one glucose syrup with a D.E. ranging from 21 to 38 and/or a maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle and
b) at least one maltodextrin with a D.E. ranging from 4 to 20 in an amount ranging from 10% to 80% by weight, preferably from 15% to 70% by weight, more preferentially from 20% to 65% by weight and better still from 40% to 60% by weight relative to the total weight of the envelope of the particle.

According to a particularly preferred form of the invention, the envelope of the encapsulation particles is formed from
a) at least one starch ($C_5$-$C_{20}$)alkenyl succinate in an amount ranging from 20% to 90% by weight, especially from 30% to 80% by weight, preferably from 40% to 70% by weight and better still from 40% to 60% by weight relative to the total weight of the envelope of the particle, and
b) at least one glucose syrup with a D.E. ranging from 21 to 38 in an amount ranging from 10% to 80% by weight, preferably from 15% to 70% by weight, more preferentially from 20% to 65% by weight and better still from 40% to 60% by weight relative to the total weight of the envelope of the particle.

Process for Preparing the Particles with Release of Beneficial Agent

The particles according to the invention may especially be prepared according to the process described in patent EP 1 917 098 B1 from FeyeCon.

According to a particular form of the invention, the particles are obtained according to a process comprising at least the following steps:
an aqueous solution formed from a mixture of the water-soluble carbohydrate and/or the water-soluble polyol and of the hydrophobically modified polysaccharide is prepared, the beneficial agent is then added and the whole is stirred so as to form an emulsion; and
said emulsion thus formed is homogenized at high pressure at a pressure ranging from 10 to 200 bar and more preferentially from 20 to 200 bar;
said emulsion is sprayed, preferably continuously, in a drying chamber; and
the water is extracted for a time preferably not exceeding 3 hours, and more preferentially not exceeding 30 minutes, with a fluid under pressure such as carbon dioxide, preferably in supercritical form, preferably at a pressure of at least 0.3 XPc and at a temperature of at least Tc−60° C. with Pc corresponding to the critical pressure of the gas and Tc the critical temperature of the gas, so as to obtain particles, which are preferably spherical, with a mean size preferably ranging from 1 to 150 μm, more preferentially ranging from 2 to 100 μm and better still from 5 to 80 μm.

Oily Phase

The composition comprises at least one oily phase, especially in a proportion of from 70% to 99.9% by weight relative to the weight, preferably from 80% to 99.7% and better still from 90% to 99.5% by weight relative to the total weight of the composition.

The oily phase generally comprises at least one volatile oil and/or one nonvolatile oil.

The term "oil" means a fatty substance that is liquid at room temperature (25° C.) and atmospheric pressure (760 mmHg, i.e. $10^5$ Pa). The oil may be volatile or nonvolatile.

For the purposes of the invention, the term "volatile oil" means an oil that is capable of evaporating on contact with the skin or the keratin fiber in less than one hour, at room temperature and atmospheric pressure. The volatile oils of the invention are volatile cosmetic oils, which are liquid at room temperature, having a nonzero vapor pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "nonvolatile oil" means an oil that remains on the skin or the keratin fiber at room temperature and atmospheric pressure for at least several hours, and that especially has a vapor pressure of less than $10^{-3}$ mmHg (0.13 Pa).

The oil may be chosen from all the physiologically acceptable and in particular cosmetically acceptable oils, especially mineral, animal, plant and synthetic oils; in particular volatile or nonvolatile hydrocarbon-based, and/or silicone and/or fluoro oils, and mixtures thereof.

More specifically, the term "hydrocarbon-based oil" means an oil mainly comprising carbon and hydrogen atoms and possibly one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oil that may be used in the invention, mention may be made of:
volatile hydrocarbon-based oils chosen from hydrocarbon-based oils containing from 8 to 16 carbon atoms, and especially C8-C16 isoalkanes of petroleum origin (also known as isoparaffins), for instance isododecane (also known as 2,2,4,4,6-pentamethylheptane), isodecane and isohexadecane, for example the oil sold under the trade names Isopar or Permethyl, branched C8-C16 esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in patent application DE10 2008 012 457 from the company Cognis.
volatile silicones, for instance linear or cyclic volatile silicone oils, in particular those with a viscosity of 8 centistokes ($8\times10^{-6}$ m$^2$/s) and especially containing from 2 to 7 silicon atoms, these silicones optionally comprising alkyl or alkoxy groups containing from 1 to 10 carbon atoms. As volatile silicone oil that may be used in the invention, mention may be made especially of octamethyl-cyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane; and mixtures thereof.

Mention may also be made of linear volatile alkyltrisiloxane oils of general formula (I):

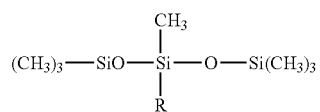

in which R represents an alkyl group comprising from 2 to 4 carbon atoms, one or more hydrogen atoms of which can be replaced by a fluorine or chlorine atom. Among the oils of general formula (I), mention may be made of: 3-butyl-1,1,1,3,5,5,5-heptamethyltrisiloxane, 3-propyl-1,1,1,3,5,5,5-heptamethyltrisiloxane, and 3-ethyl-1,1,1,3,5,5,5-heptamethyltrisiloxane, corresponding to the oils of formula (I) for which R is, respectively, a butyl group, a propyl group or an ethyl group.

As examples of nonvolatile oil that may be used in the invention, mention may be made of:
hydrocarbon-based oils of animal origin, such as perhydrosqualene;
hydrocarbon-based plant oils such as liquid triglycerides of fatty acids of 4 to 24 carbon atoms, for instance heptanoic or octanoic acid triglycerides, or wheatgerm oil, olive oil, sweet almond oil, palm oil, rapeseed oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passion flower oil, musk rose oil, sunflower oil, corn oil, soybean oil, grapeseed oil, sesame seed oil, hazelnut oil, apricot oil, macadamia oil, castor oil, avocado oil, and caprylic/capric acid triglycerides, for instance those sold by the company Stéarineries Dubois or those sold under the names Miglyol 810, 812 and 818 by the company Dynamit Nobel;
linear or branched hydrocarbons, of mineral or synthetic origin, such as liquid paraffins and derivatives thereof, petroleum jelly, polydecenes, polybutenes, hydrogenated polyisobutene such as Parleam, or squalane;
synthetic ethers containing from 10 to 40 carbon atoms;
synthetic esters, especially of fatty acids, for instance the oils of formula $R_1COOR_2$ in which $R_1$ represents a linear or branched higher fatty acid residue containing from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alcohol benzoates, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate;
fatty alcohols which are liquid at room temperature, comprising a branched and/or unsaturated carbon chain having from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates, such as diethylhexyl carbonate;

acetates;

citrates;

partially hydrocarbon-based and/or silicone-based fluoro oils such as fluorosilicone oils, fluorinated polyethers and fluorosilicones as described in document EP-A-847 752;

silicone oils such as linear or cyclic nonvolatile polydimethylsiloxanes (PDMSs); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

The composition according to the invention may also comprise fatty substances other than the above oils, which may be chosen by a person skilled in the art on the basis of his general knowledge, so as to give the final composition the desired properties, for example in terms of consistency and/or texture.

These additional fatty substances may be waxes, gums and/or pasty fatty substances of animal, plant, mineral or synthetic origin, and also mixtures thereof.

For the purposes of the present invention, a wax is a lipophilic fatty compound, which is solid at room temperature (25° C.) with a reversible solid/liquid change of state, having a melting point greater than 40° C., which may be up to 200° C., generally a hardness greater than 0.5 MPa, and having an anisotropic crystal organization in the solid state.

Mention may be made especially of waxes of animal, plant, mineral or synthetic origin such as microcrystalline waxes, paraffin wax, petrolatum, petroleum jelly, ozokerite, montan wax; beeswax, lanolin wax and derivatives thereof; candelilla wax, ouricury wax, carnauba wax, Japan wax, cocoa butter, cork fiber wax or sugarcane wax, lignite wax, rice bran wax, fir tree wax, cotton wax; hydrogenated oils with a melting point greater than 40° C. (approximately), such as hydrogenated jojoba oil;

fatty esters and glycerides that are concrete at 25° C.; polyethylene waxes and the waxes obtained by Fischer-Tropsch synthesis; hydrogenated oils that are concrete at 25° C.; lanolins.

The pasty fatty substances generally have a melting point of between 25 and 60° C., preferably between 30 and 45° C., and/or a hardness ranging from 0.001 and 0.5 MPa, preferably between 0.005 and 0.4 MPa. Mention may be made especially of lanolins and derivatives thereof, or cholesterol esters.

Beneficial Agents

The amount of beneficial agent present in the particles in accordance with the invention preferably ranges from 0.1% to 80% by weight relative to the weight of the particle, preferably from 1% to 70% by weight, better still from 10% to 60% and even better still from 15% to 50% by weight relative to the total weight of the particle.

The time for release of the beneficial agent will obviously vary according to the nature and intensity of the stimulus.

The total duration for release of the beneficial agent may be modified and will depend greatly on the composition of the oil of the content of particles present in the oil, the nature and especially the chemical nature of the beneficial agent and its concentration in the particles (amount encapsulated in the particle) and the nature and intensity of the stimulus to which the particle containing the beneficial agent will be subjected. The release may equally be instantaneous or last several hours or even several days.

Among the beneficial agents that may be used according to the invention, mention may be made more particularly of:
(i) fatty substances;
(ii) fragrancing substances;
(iii) pharmaceutical active principles;
(iv) cosmetic active agents.

Fatty Substances

They may be chosen from the group comprising
(i) natural oils of plant, animal or marine origin,
(ii) mineral oils,
(iii) hydrogenated oils,
(iv) silicone oils,
(v) terpenes,
(vi) squalene,
(vii) saturated or unsaturated fatty acids,
(viii) fatty acid esters,
(x) waxes,
(x) fatty alcohols,
(xi) butters such as shea butter or cocoa butter,
(xii) and mixtures thereof.

Fragrancing Substances

The term "fragrancing substance" means any ingredient that is capable of giving off a pleasant odor.

Perfumes are compositions especially containing starting materials (generally referred to as perfumery ingredients) described in S. Arctander, Perfume and Flavor Chemicals (Montclair, N.J., 1969), in S. Arctander, Perfume and Flavor Materials of Natural Origin (Elizabeth, N.J., 1960) and in Flavor and Fragrance Materials—1991, Allured Publishing Co., Wheaton, Ill.

They may be synthesis products or natural products, for instance essential oils, absolutes, resinoids, resins, concretes, and/or synthetic products (terpene or sesquiterpene hydrocarbons, alcohols, phenols, aldehydes, ketones, ethers, acids, esters, nitriles or peroxides, which may be saturated or unsaturated, and aliphatic or cyclic).

According to the definition given in international standard ISO 9235 and adopted by the Commission of the European Pharmacopoeia, an essential oil is an odoriferous product generally of complex composition, obtained from a botanically defined plant raw material, either by steam entrainment, or by dry distillation, or via an appropriate mechanical process without heating. The essential oil is generally separated from the aqueous phase via a physical process which does not result in any significant change in the composition.

Among the essential oils that may be used according to the invention, mention may be mode of those obtained from plants belonging to the following botanical families:

Abietaceae or Pinaceae: conifers; Amaryllidaceae; Anacardiaceae; Anonaceae: ylang ylang; Apiaceae (for example Umbelliferae): dill, angelica, coriander, sea fennel, carrot, parsley; Araceae; Aristolochiaceae; Asteraceae: yarrow, artemisia, camomile, helichrysum; Betulaceae; Brassicaceae; Burseraceae: frankincense; Caryophyllaceae; Canellaceae; Cesalpiniaceae: copaifera (copaiba balsam); Chenopodaceae; Cistaceae: rock rose; Cyperaceae; Dipterocarpaceae; Ericaceae: gaultheria (wintergreen); Euphorbiaceae; Fabaceae; Geraniaceae: geranium; Guttiferae; Hamamelidaceae; Hernandiaceae; Hypericaceae: St John's wort; Iridaceae; Juglandaceae; Lamiaceae: thyme, oregano, monarda, savory, basil, marjorams, mints, patchouli, lavenders, sages, catnip, rosemary, hyssop, balm; Lauraceae: ravensara, sweet bay, rosewood, cinnamon, litsea; Liliaceae: garlic; lily, lily of the valley, hyacinth, daffodil; Magnoliaceae: magnolia; Malvaceae; Meliaceae; Monimiaceae; Moraceae: hemp, hop; Myricaceae; Myristicaceae: nutmeg; Myrtaceae: eucalyptus, tea tree, paperbark tree, cajuput, backhousia, clove, myrtle; Oleaceae; Piperaceae: pepper; Pittosporaceae; Poaceae: lemon balm, lemongrass, vetiver; Polygonaceae; Renonculaceae; Rosaceae: roses; Rubiaceae; Rutaceae: all citrus plants; Salicaceae; Santalaceae: sandalwood; Saxifragaceae; Schisandraceae; Styracaceae: benzoin; Thymelaceae: agarwood; Tilliaceae; Valerianaceae: valerian, spikenard; Verbenaceae: lantana, verbena; Violaceae; Zingiberaceae: galangal, turmeric, cardamom, ginger; Zygophyllaceae.

Mention may also be made of the essential oils extracted from flowers (lily, lavender, rose, jasmine, ylang ylang, neroli), from stems and leaves (patchouli, geranium, petitgrain), from fruit (raspberry, peach, coriander, aniseed, cumin, juniper), from fruit peel (bergamot, lemon, orange, grapefruit), from roots (angelica, celery, cardamom, iris, sweet flag, ginger), from wood (pinewood, sandalwood, gaiac wood, rose of cedar, camphor), from grasses and gramineae (tarragon, rosemary, basil, lemongrass, sage, thyme), from needles and branches (spruce, fir, pine, dwarf pine) and from resins and balms (galbanum, elemi, benzoin, myrrh, olibanum, opopanax).

Examples of fragrancing substances are especially: geraniol, geranyl acetate, farnesol, borneol, bornyl acetate, linolool, linalyl acetate, linalyl propionate, linalyl butyrate, tetrahydrolinolool, citronellol, citronellyl acetate, citronellyl formate, citronellyl propionate, dihydromyrcenol, dihydromyrcenyl acetate, tetrahydromyrcenol, terpineol, terpinyl acetate, nopol, nopyl acetate, nerol, neryl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, cis-3-hexenyl acetate, vetiveryl acetate, ethyl acetate, butyl acetate, hexyl acetate, decyl acetate, isoamyl acetate, stearyl acetate, allyl heptanoate, vetiverol, α-hexylcinnamaldehyde, 2-methyl-3-(p-tert-butylphenyl) propanal, 2-methyl-3-(p-isopropylphenyl)propanal, 3-(p-tert-butylphenyl)propanal, 2,4-dimethylcyclohex-3-enylcarboxaldehyde, tricyclodecenyl acetate, tricyclodecenyl propionate, allyl 3-cyclohexylpropionate, ethyl 6-(acetyloxy)hexanoate, allyl caproate, ethyl 2-m ethylbutyrate, methyl dihydrojasmonate, hexyl salicylate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-4-heptylcyclopentanone, 3-methyl-2-pentyl-2-cyclopentenone, menthone, carvone, tagetone, geranyl acetone, n-decanal, n-dodecanal, anisylpropanal, 9-decen-1-ol, cis-3-hexenol, tetrahydro-2-isobutyl-4-methylpyran-4-ol, 3-methyl-5-phenyl-1-pentanol, 3a,6,6,9a-tetramethyldodecahydronaphtho[2,1-b]furan, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepinonitrile, aubepine, heliotropin, coumarin, eugenol, vanillin, diphenyl ether, citral, citronellal, hydroxycitronellal, hexylcinnamal, 2,4-dimethylcyclohex-3-ene-1-carbaldehyde, 2,6-dimethylhept-5-enal, α,α-dimethyl-p-ethylphenylpropanal, 1,3-benzodioxole-5-carboxaldehyde, limonene, damascone, decalactone, nonalactone, 6,6-dimethoxy-2,5,5-trimethylhex-2-ene, 2,4,4,7-tetramethyloct-6-en-3-one, 1-(5,5-dimethyl-1-cyclohexenyl) pent-4-en-1-one, methylheptenone, 4-(cyclopropylmethyl) phenyl methyl ether, 2-methyl-6-methylideneoct-7-en-2-ol, rose oxide, 1-(1,2,3,4,5,6,7,8-octahydro-2,3,8,8-tetramethyl-2-naphthyl)ethan-1-one, 2-acetonaphthone, 2-isopropyl-5-methylcyclohexanone, ionones, methylionones, isomethylionones, solanone, irones, cis-3-hexenol and esters thereof, indane musks, tetralin musks, isochroman musks, macrocyclic ketones, macrolactone musks, aliphatic musks, ethylene brassylate, rose essence, and mixtures thereof.

In general, perfumes are formed from a mixture of perfumery ingredients which may also be classified into head notes, heart notes and base notes.

The three notes correspond to the greater or lesser volatility of the ingredients of which they are composed: highly volatile head note, moderately volatile heart note and sparingly volatile base note.

(i) The head note, also known as the "top" note, is that which is first perceived by the sense of smell as soon as the perfume comes into contact with the keratin material or any substrate. However, it is the note which fades the fastest: it does not "last". It is difficult to express the time of persistence of this note, since it is very variable: from a few minutes to about 10 minutes.

It is essentially fresh and light. All the citrus notes especially fall into this category. In perfumery, they are grouped under the generic term hesperidean notes, which include orange, lemon, grapefruit, bergamot, neroli, etc. Mention will also be made of herbal notes such as lavender, laurel, thyme or rosemary, and aniseed, menthol, aldehyde, etc. notes. Mention will also be made of eucalyptus notes.

(ii) The heart note, also occasionally referred to as the "body note", has a persistence which lasts from a few tens of minutes to a few hours, but its main characteristic is that it is not perceived until after a few minutes. Thus, it "starts" just before the head note dies off. It begins to express itself while the head note is gradually fading away. It is represented essentially by floral, fruity or spicy scents: lily of the valley, honeysuckle, violet, magnolia, cinnamon, geranium, jasmine, rose, iris, raspberry, peach, etc.

(ii) The base note, also occasionally known as the "bottom note", gives a perfume its "durability", persistence or staying power. It is perceptible several hours, or even several days, or even several weeks after application onto clothing or a perfume blotter or scent strip, depending on the concentration of the perfume. Examples that will be mentioned include woods, roots, mosses and resins and animal or mineral substances such as opoponax, musks, amber, sandalwood, benzoin, lichen, clove, sage, etc. Mention will also be made of vanilla, patchouli, coumarin, etc. notes.

Needless to say, ingredients belonging to one or more notes may be encapsulated. However, it will be preferred to encapsulate the most volatile ingredients (i.e. the least persistent) belonging to the head and/or heart notes. Among these ingredients, examples that will be mentioned include:
benzyl acetate
geranyl acetate
cis-3-hexenyl acetate
C18 aldehyde or nonalactone
decyl acetate
allyl amyl glycolate (citral)
ethyl acetate
butyl acetate
allyl 3-cyclohexylpropionate
linalyl acetate
phenylethyl alcohol
hexyl acetate
Berryflor or ethyl 6-(acetyloxy)hexanoate
isoamyl acetate allyl caproate
Amarocite or 6,6-dimethoxy-2,5,5-trimethylhex-2-ene
Citral Lemarome N or 3,7-dimethylocta-2,6-dienal
Canthoxal or anisylpropanal
Claritone or 2,4,4,7-tetramethyloct-6-en-3-one
ethyl 2-methylbutyrate
dihydromyrcenol
cis-3-hexenol
Hedione or methyl dihydrojasmonate
L-carvone
allyl heptanoate
limonene
Neobutenone Alpha or 1-(5,5-dimethyl-1-cyclohexenyl)pent-4-en-1-one
Methylheptenone
Toscanol or 4-(cyclopropylmethyl)phenyl methyl ether
Myrcenol Super or 2-methyl-6-methylideneoct-7-en-2-ol
decalactone
stearyl acetate
rose oxide
linalool
Triplal or 2,4-dimethylcyclohex-3-ene-1-carbaldehyde
Melonal or 2,6-dimethylhept-5-enal
1-(1,2,3,4,5,6,7,8-octahydro-2,3,8,8-tetramethyl-2-naphthyl)ethan-1-one
hexylcinnamal
tetrahydro-2-isobutyl-4-methylpyran-4-ol
hexyl salicylate
1,4-dioxacycloheptadecane-5,17-dione
and mixtures thereof.

According to a particular form of the invention, encapsulation particles comprise at least one or more fragrancing substances with a saturating vapor pressure at 25° C. of greater than or equal to 10.0 Pa.

The saturating vapor pressure (or vapor tension) is the pressure at which the gaseous phase of a substance is in equilibrium with its liquid or solid phase at a given temperature in a closed system. Calculation of the saturating vapor pressure may be performed using the following formula:

$$\ln \frac{p_{sat}}{p_0} = \frac{M \cdot L_v}{R}\left(\frac{1}{T_0} - \frac{1}{T}\right)$$

with:
- $T_0$: boiling point of the substance at a given pressure $p_0$, in degrees Kelvin,
- $p_{sat}$: saturating vapor pressure, in the same unit as $p_0$
- M: molar mass of the substance, in kg/mol
- $L_v$: latent heat of vaporization of the substance, in joules/kg
- R: ideal gas constant, equal to 8.31447 J/K/mol
- T: temperature of the vapor, in K.

Preferably, the fragrancing substances with a saturating vapor pressure at 25° C. of greater than or equal to 10 Pa represent an amount ranging from 50% to 100% by weight, preferably from 60% to 100% by weight, more preferentially from 70% to 100% by weight and better still from 80% to 100% by weight relative to the total weight of the fragrancing substances present in the particles of the invention.

a) Pharmaceutical Active Principles
The term "pharmaceutical active principle" means a molecule or a mixture of molecules which has a curative and/or prophylactic therapeutic effect, which can be administered by spraying.

b) Cosmetic Active Agents
The term "cosmetic active agent" means any molecule which has a hygiene, care, makeup or coloring effect contributing toward the improvement well-being and/or enhancement or modification of the appearance of the human keratin material onto which said composition is applied.

Among the cosmetic active agents that may be applied to human keratin materials such as the skin, the lips, the scalp, the hair, the eyelashes or the nails, examples that may be mentioned, alone or as mixtures, include:
- vitamins and derivatives or precursors thereof, alone or as mixtures;
- antioxidants;
- cleaning agents such as surfactants;
- dyestuffs;
- conditioning agents;
- agents for relaxing and/or straightening and/or shaping the hair;
- free-radical scavengers;
- photoprotective agents such as organic or mineral UV-screening agents;
- self-tanning agents;
- anti-glycation agents;
- calmatives;
- hair-removing agents;
- deodorant agents;
- antiperspirant agents;
- NO-synthase inhibitors;
- agents for stimulating fibroblast proliferation;
- agents for stimulating keratinocyte proliferation;
- dermo-relaxing agents,
- refreshing agents;
- tensioning agents,
- matt-effect agents;
- skin-shine counteractants;
- dermorelaxing agents;
- antiseborrhea agents;
- greasy-hair counteractants;
- depigmenting agents;
- pro-pigmenting agents;
- keratolytic agents;
- desquamating agents;
- moisturizers;
- antimicrobial agents;
- slimming agents;
- agents that act on the energy metabolism of cells;
- insect repellents;
- substance P or CGRP antagonists;
- hair-loss counteractants;
- antiwrinkle agents;
- antiaging agents;
- antidandruff agents.

Among these cosmetic active agents, preference will be given most particularly, alone or as mixtures, to:
- photoprotective agents such as UV-screening agents, in particular organic UV-screening agents;
- skin-shine counteractants;
- dermorelaxing agents;
- antiseborrhea agents;
- greasy-hair counteractants;
- deodorant agents;
- antiperspirant agents;
- refreshing agents;
- matt-effect agents;
- antimicrobial agents;
- antidandruff agents.

According to a particularly preferred form of the invention, the beneficial agent(s) present in the particles will be chosen from fragrancing substances.

According to an even more particularly preferred form of the invention, the fragrancing substances present in the particles are chosen from heart notes and/or head notes so as to be able both to compensate for their loss throughout the day and to afford an additional freshness effect throughout the day in response to perspiration or to atmospheric humidity or humidity provided, for example, by misters.

According to a particular form of the invention, the composition will contain
a) particles containing at least one fragrancing substance and
b) at least one fragrancing substance in free form, which may be identical to or different from the fragrancing substance present in said particles.

Said fragrancing substances in free form may be chosen from those mentioned previously.

According to another particular form of the invention, the composition exclusively contains the fragrancing substance(s) in the encapsulation particles. In other words, all of the ingredients for fragrancing that are present in the composition are contained in the particles.

The composition may also comprise other ingredients in free form (not encapsulated or imprisoned in the particles of the invention) used commonly in cosmetic compositions. Such ingredients may be chosen from antioxidants, preserving agents, cosmetic active agents such as those mentioned previously, fragrancing substances such as those described previously, surfactants, spreading agents, wetting agents, dispersants, antifoams, neutralizers, stabilizers, polymers and especially liposoluble film-forming polymers, and mixtures thereof.

Needless to say, those skilled in the art will take care to select this or these optional additional compound(s) and/or the amounts thereof so that the advantageous properties of the composition for the use according to the invention are not, or are not substantially, adversely affected by the envisaged addition.

The compositions according to the invention may be in any form that is acceptable and common for a composition in the form of oil.

A person skilled in the art can choose the appropriate composition, and also its method of preparation, on the basis of his general knowledge, taking into account first the nature of the constituents used, especially their solubility in the support, and secondly the application envisaged for the composition.

According to a particular form of the invention, the compositions according to the invention are skincare products especially for the face or the lips, in which the composition comprises at least one cosmetic or dermatological active agent. These products may especially be antisun oils, self-tanning oils or massage oils. More particularly, the particles comprise at least one fragrancing substance. Even more particularly, the compositions will also contain a fragrancing substance in free form, which may be identical to or different from the fragrancing substance present in the particles.

According to another particular form of the invention, the compositions according to the invention may be in the form of hair products. These hair products may especially be care, conditioning or styling products. More particularly, the particles comprise at least one fragrancing substance. Even more particularly, the compositions will also contain a fragrancing substance in free form, which may be identical to or different from the fragrancing substance present in the particles.

According to another particular form of the invention, the compositions according to the invention may be in the form of deodorant and/or antiperspirant products in which the composition comprises at least one deodorant active agent and/or at least one antiperspirant active agent in free form and/or in encapsulated form. More particularly, the particles comprise at least one fragrancing substance. Even more particularly, the compositions will also contain a fragrancing substance in free form, which may be identical to or different from the fragrancing substance present in the particles.

Antiperspirant Active Agent

The term "antiperspirant active agent" means a compound which, by itself, has the effect of reducing the flow of sweat and/or of reducing the sensation on the skin of moisture associated with human sweat and/or of partially or totally absorbing human sweat.

Among the antiperspirant active agents that may be mentioned are aluminum and/or zirconium salts such as aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, alum salts, aluminum sulfate, aluminum zirconium octachlorohydrate, aluminum zirconium pentachlorohydrate, aluminum zirconium tetrachlorohydrate, aluminum zirconium trichlorohydrate and more particularly the aluminum chlorohydrate in activated or nonactivated form sold by the company Reheis under the name Microdry Aluminum Chlorohydrate® or by the company Guilini Chemie under the name Aloxicoll PF 40. Aluminum and zirconium salts are, for example, the product sold by the company Reheis under the name Reach AZP-908-SUF®, "activated" aluminum salts, for example the product sold by the company Reheis under the name Reach 103 or by the company Westwood under the name Westchlor 200.

Preferably, the cosmetic composition comprises aluminum chlorohydrate as antiperspirant active agent.

As other antiperspirant active agent, mention may be made of expanded perlite particles such as those obtained by the expansion process described in U.S. Pat. No. 5,002,698.

The perlites that may be used according to the invention are generally aluminosilicates of volcanic origin and have the composition:
70.0%-75.0% by weight of silica $SiO_2$
12.0%-15.0% by weight of aluminum oxide $Al_2O_3$
3.0%-5.0% of sodium oxide $Na_2O$
3.0%-5.0% of potassium oxide $K_2O$
0.5%-2% of iron oxide $Fe_2O_3$
0.2%-0.7% of magnesium oxide MgO
0.5%-1.5% of calcium oxide CaO
0.05%-0.15% of titanium oxide $TiO_2$.

Preferably, the perlite particles used will be ground; in this case, they are known as Expanded Milled Perlite (EMP). They preferably have a particle size defined by a median diameter D50 ranging from 0.5 to 50 μm and preferably from 0.5 to 40 μm.

Preferably, the perlite particles used have a loose bulk density at 25° C. ranging from 10 to 400 kg/m³ (standard DIN 53468) and preferably from 10 to 300 kg/m³.

Preferably, the expanded perlite particles according to the invention have a water absorption capacity, measured at the wet point, ranging from 200% to 1500% and preferably from 250% to 800%.

The wet point corresponds to the amount of water which has to be added to 100 g of particle in order to obtain a homogeneous paste. This method is directly derived from the oil uptake method applied to solvents. The measurements are taken in the same manner by means of the wet point and the flow point, which have, respectively, the following definitions:

Wet point: weight, expressed in grams per 100 g of product, corresponding to the production of a homogeneous paste during the addition of a solvent to a powder.

Flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol:
Protocol for Measuring the Water Absorption
1) Equipment Used
Glass plate (25×25 mm)
Spatula (wooden shaft and metal part, 15×2.7 mm)
Silk-bristled brush
Balance
2) Procedure The glass plate is placed on the balance and 1 g of perlite particles is weighed out. The beaker containing the solvent and the sampling pipette is placed on the balance. The solvent is gradually added to the powder, the whole being regularly blended (every 3 to 4 drops) by means of the spatula.

The mass of solvent needed to obtain the wet point is noted. Further solvent is added and the mass which makes it possible to reach the flow point is noted. The average of three tests will be determined.

The expanded perlite particles sold under the trade names Optimat 1430 OR or Optimat 2550 by the company World Minerals will be used in particular.
Deodorant Active Agents The term "deodorant active agent" refers to any substance that is capable of masking, absorbing, improving and/or reducing the unpleasant odor resulting from the decomposition of human sweat by bacteria.

The deodorant active agents may be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts; polyols such as those of glycerol type, 1,3-propanediol (Zemea Propanediol® sold by DuPont Tate & Lyle Bio Products), 1,2-decanediol (Symclariol® from the company Symrise), glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), biguanide derivatives, for instance polyhexamethylene biguanide salts; chlorhexidine and salts thereof; 4-phenyl-4,4-dimethyl-2-butanol (Symdeo MPP® from Symrise); cyclodextrins; chelating agents such as Tetrasodium Glutamate Diacetate (CAS #51981-21-6) sold under the trade name Dissolvine GL-47-S® from AkzoNobel, EDTA (ethylenediaminetetraacetic acid) and DPTA (1,3-diaminopropanetetraacetic acid).

Among the deodorant active agents in accordance with the invention, mention may also be made of:

zinc salts, such as zinc salicylate, zinc phenolsulfonate, zinc pyrrolidonecarboxylate (more commonly known as zinc pidolate), zinc sulfate, zinc chloride, zinc lactate, zinc gluconate, zinc ricinoleate, zinc glycinate, zinc carbonate, zinc citrate, zinc chloride, zinc laurate, zinc oleate, zinc orthophosphate, zinc stearate, zinc tartrate, zinc acetate or mixtures thereof;

odor absorbers such as zeolites, especially silver-free metal zeolites, cyclodextrins, metal oxide silicates such as those described in patent application US 2005/063 928; metal oxide particles modified with a transition metal, as described in patent applications US 2005/084 464 and US 2005/084 474, aluminosilicates such as those described in patent application EP 1 658 863, chitosan-based particles such as those described in patent U.S. Pat. No. 6,916,465;

sodium bicarbonate;

salicylic acid and derivatives thereof such as 5-n-octanoylsalicylic acid;

alum;

triethyl citrate;

The deodorant active agents may preferably be present in the compositions according to the invention in weight proportions of from 0.01% to 10% by weight relative to the total weight of the composition.

The invention also relates to a cosmetic process for treating body odor and optionally human perspiration, which consists in applying to a keratin material a composition comprising particles as defined previously; said composition comprising at least one deodorant active agent and/or at least one antiperspirant active agent in free form and/or in encapsulated form.

The invention is illustrated in greater detail in the examples that follow.

EXAMPLES OF PREPARING PARTICLES WITH RELEASE OF PERFUME

Example A

Capsules were prepared using the following composition:

|  | Composition | | | |
|---|---|---|---|---|
|  | Hydrophobically modified starch | Water-soluble polysaccharide | Perfume * | Water |
| Example A | Amidon Capsul ® from National Starch 110 g | Potato maltodextrin MD 20 P from Avebe 110 g | 55 g | 225 g |

| Ingredients | Amount in g |
|---|---|
| Isopropyl myristate | 20.5 |
| Methyl dihydrojasmonate | 15 |
| 2-Phenylethanol | 8 |
| 1-(1,2,3,4,5,6,7,8-Octahydro-2,3,8,8-tetramethyl-2-naphthyl)ethan-1-one | 8 |
| Hexylcinnamal | 6 |
| Tetrahydro-2-isobutyl-4-methylpyran-4-ol | 6 |
| Hexyl salicylate | 6 |
| Benzyl acetate | 5 |
| 1,4-Dioxacycloheptadecane-5,17-dione | 5 |

| Ingredients | Amount in g |
|---|---|
| 3-Methyl-5-phenyl-1-pentanol | 5 |
| Dihydromyrcenol | 4 |
| Orange terpenes 0.05% B H T (limonene >95%) | 4 |
| 2-Acetonaphthone | 2 |
| 3a,6,6,9a-Tetramethyldodecahydronaphtho[2,1-b]furan | 1 |
| α,α-Dimethyl-p-ethylphenylpropanal | 1 |
| 1,3-Benzodioxole-5-carboxaldehyde | 1 |
| 2-Isopropyl-5-methylcyclohexanone | 1 |
| 1-Phenylethyl acetate | 0.8 |
| 2,6-Dimethylhept-5-enal (Melonal) | 0.5 |
| 2,4-Dimethylcyclohex-3-ene-1-carbaldehyde (Triplal) | 0.2 |

Process for Preparing the Emulsion

Potato maltodextrin MD20 P and Amidon Capsul® (sodium salt of starch octenyl succinate) were mixed in water until dissolved, the perfume was then added and the whole was emulsified with a Heidolph Diax 900 Ultra-Turrax disperser (motor power 900 W with an electronically controlled speed of 8000 to 26 000 rpm) at the maximum power for 4 minutes.

Drying Procedure for Obtaining Spherical Particles

The emulsion obtained was then homogenized at a pressure of 30 bar using a high-pressure pump and then sprayed in an atomization chamber using a nozzle simultaneously with a stream of $CO_2$ (30 bar, 45° C.) which was circulated continuously at a flow rate of about 500 g/min to remove the water. The dried powder was retained on a filter located at the base of the atomization chamber, and then collected after depressurization. 270 g of spherical microcapsules are thus obtained in the form of a fine white powder with a number-mean diameter of 7.8 μm and a volume-mean diameter of 47 μm.

The size of the particles was measured via a dry route by laser scattering using a Microtrac S3500 particle size analyzer, the particle sizes being expressed by volume and by number.

Measured characteristics of the capsules

| | Amount of encapsulated perfume (%) | Amount of free perfume (%) | Poured powder density | Absolute density |
|---|---|---|---|---|
| Example A | 19.8 | <0.1 | 484 | 1.12 |

Examples B to H

According to the process described in Example A, the following capsules were prepared:

| Composition | Hydrophobically modified starch | Water-soluble polysaccharide | Perfume of Example A | Water |
|---|---|---|---|---|
| Example B | Amidon Capsul® from National Starch 110 g | Maltodextrin MD 120 from Tereos 110 g | 55 g | 225 g |
| Example C | Amidon Capsul® from National Starch 110 g | Maltodextrin MD 170 from Tereos 110 g | 55 g | 225 g |
| Example D | Amidon Capsul® from National Starch 110 g | Maltodextrin MD 190 from Tereos 110 g | 55 g | 225 g |
| Example E | Amidon Capsul® from National Starch 110 g | Potato maltodextrin MD 20 P from Avebe 110 g | 105 g | 225 g |
| Example F | Amidon Capsul® from National Starch 154 g | Potato maltodextrin MD 20 P from Avebe 66 g | 55 g | 225 g |
| Example G | Amidon Capsul® from National Starch 66 g | Potato maltodextrin MD 20 P from Avebe 154 g | 55 g | 225 g |
| Example H | Amidon Capsul® from National Starch 110 g | Glucose syrup Glucodry G290 from Tereos 110 g | 55 g | 225 g |

Measured characteristics of the capsules

| Examples | Amount of encapsulated perfume (%) | Amount of free perfume (%) | Poured powder density (g/l) | Absolute density |
|---|---|---|---|---|
| Example B | 19.3 | <0.1 | 568 | 1.14 |
| Example C | 19.4 | <0.1 | 490 | 1.16 |
| Example D | 19.9 | <0.1 | 537 | 1.11 |
| Example E | 38 | 0.8 | 482 | 1.08 |
| Example F | 21.0 | 0.2 | 595 | 1.11 |
| Example G | 20.7 | 0.2 | 521 | 1.15 |
| Example H | 19.2 | 0.1 | 568 | 1.12 |

Comparative Example I

Capsules having the same composition as Example A as described above were prepared according to the process of Example 1 of patent U.S. Pat. No. 6,200,949 comprising drying by spray-drying (atomization) of the emulsion.

The emulsion is dried by spray-drying using a Bowen Lab Model Dryer machine using air with a flow rate of 420 m³/h at a temperature of 204° C. and an external temperature of 93° C. and a turbine speed of 50 000 rpm.

Morphological aspect of the particles obtained: polymorphous with aggregates

Comparative Example J

Capsules having the same composition as Example A as described above were prepared according to the process of Example 1 of patent U.S. Pat. No. 5,508,259 comprising drying by spray-drying (atomization) of the emulsion etc.

The mixture was dried by spray-drying with a CCM Sulzer machine at an emulsion flow rate of 50 kg/h, air at a flow rate of 320 m³/h at 350° C. and 0.45 bar.

Morphological aspect of the particles obtained: polymorphous with aggregates

| Composition | Measured characteristics of the capsules | | | |
|---|---|---|---|---|
| | Amount of encapsulated perfume (%) | Amount of free perfume (%) | Poured powder density (g/l) | Absolute density |
| Example I (outside the invention) | 18.3 | 2.7 | 259 | 1.16 |
| Example J (outside the invention) | 11.2 | 1.7 | 269 | 1.12 |

Example 1: Antisun Oil

An antisun oil having the following composition was prepared:

| Ingredients | (weight %) |
|---|---|
| Cyclopentadimethylsiloxane | 20 |
| Castor oil | 1.8 |
| 2-Ethylhexyl 4-hydroxycinnamate | 0.1 |
| Perfume capsules of Example A | 0.6 |
| Isopropyl palmitate | qs |
| Total | 100.00 |

10.0 g of cyclopentadimethylsiloxane, 0.9 g of castor oil, 0.05 g of ethylhexyl hydroxycinnamate and 38.75 g of isopropyl palmitate are placed in a tank equipped with a stirrer.

The mixture is homogenized with vigorous stirring (1000 rpm). 0.3 g of capsules of Example A is then added. The mixture is homogenized again with vigorous stirring (1000 rpm). A yellowish-white liquid was thus obtained.

Comparative Examples C1 and C2: Antisun Oils

In a manner similar to that of Example 1, anhydrous antisun oils having the following compositions were prepared:

Example C1

| Ingredients | (weight %) |
|---|---|
| Cyclopentadimethylsiloxane | 20 |
| Castor oil | 1.8 |
| 2-Ethylhexyl 4-hydroxycinnamate | 0.1 |
| Perfume capsules of Example I | 0.6 |
| Isopropyl palmitate | qs |
| Total | 100.00 |

Example C2

| Ingredients | (weight %) |
|---|---|
| Cyclopentadimethylsiloxane | 20 |
| Castor oil | 1.8 |
| 2-Ethylhexyl 4-hydroxycinnamate | 0.1 |
| Perfume capsules of Example J | 0.6 |
| Isopropyl palmitate | qs |
| Total | 100.00 |

Evaluation Protocol

About 0.2 g of composition was deposited homogeneously onto a perfume blotter. After 1 minute, the perfume odor intensity was evaluated. Perspiration was then simulated by adding about 0.1 g of water (three sprays) onto the deposited composition. After waiting for one minute, the blotter was smelled again.

| Oil | Odor intensity BEF | Odor intensity AFT |
|---|---|---|
| Example 1 | Odorless | Strong perfume odor |
| Example C1 | Strong perfume odor | Strong perfume odor |
| Example C2 | Strong perfume odor | Strong perfume odor |

BEF = before addition of water;
AFT = after addition of water

It was thus observed at $T_0$ that the oil of Example 1 comprising the perfume capsules according to the invention has no odor before the addition of water, in contrast with oils C1 and C2 (outside the invention), which shows that the perfume capsules in oils C1 and C2 are not leaktight even before the addition of water.

It was also observed that the oil of Example, 1 after stimulation with water, led to a very intense odor, which demonstrates substantial release of perfume in response to the water stimulus.

In a manner similar to that of Example 1, anhydrous antisun oils having the following compositions were prepared:

Example 2: Antisun Oil

| Ingredients | (weight %) |
|---|---|
| Cyclopentadimethylsiloxane | 20 |
| Castor oil | 1.8 |
| 2-Ethylhexyl 4-hydroxycinnamate | 0.1 |
| Perfume capsules of Example B | 0.6 |
| Isopropyl palmitate | qs |
| Total | 100.00 |

The perfume capsules of Example B may be replaced with the capsules of Examples A and C to H described previously.

10.0 g of cyclopentadimethylsiloxane, 0.9 g of castor oil, 0.05 g of ethylhexyl hydroxycinnamate and 38.75 g of isopropyl palmitate were placed in a tank equipped with a stirrer. The mixture was homogenized with vigorous stirring (1000 rpm). 0.3 g of capsules of Example B was then added. The mixture was homogenized again with vigorous stirring (1000 rpm). A yellowish-white liquid was thus obtained.

The composition applied to the body releases perfume in the course of the day, on contact with perspiration or moisture.

Example 3: Antisun Oil

| Ingredients | (weight %) |
| --- | --- |
| Cyclopentadimethylsiloxane | 20 |
| Mineral oil | 1.8 |
| 2-Ethylhexyl 4-hydroxycinnamate | 0.1 |
| Perfume A | 0.2 |
| Perfume capsules of Example F | 0.6 |
| Isopropyl palmitate | qs |
| Total | 100.00 |

The perfume capsules of Example F may be replaced with the capsules of Examples A to E, G and H described previously.

10.0 g of cyclopentadimethylsiloxane, 0.9 g of castor oil, 0.05 g of ethylhexyl hydroxycinnamate 0.1 g of Perfume and 38.65 g of isopropyl palmitate were placed in a tank equipped with a stirrer. The mixture was homogenized with vigorous stirring (1000 rpm). 0.3 g of capsules of Example F was then added. The mixture was homogenized again with vigorous stirring (1000 rpm). A yellow-white liquid was thus obtained.

The composition applied to the body releases perfume in the course of the day, on contact with perspiration or moisture.

Example 4: Massage Oil

| Ingredients | (weight %) |
| --- | --- |
| Cyclopentadimethylsiloxane | 32 |
| Caprylic/capric triglycerides | 42.95 |
| Isopropyl palmitate | 22 |
| Perfume capsules of Example H | 1 |
| Dimethicone/trimethyl siloxysilicate | 2 |
| Di-tert-butyl-4-hydroxytoluene | 0.05 |
| Total | 100.00 |

The perfume capsules of Example H may be replaced with the capsules of Examples A to G described previously.

11.0 g of isopropyl palmitate, 16.0 g of cyclopentadimethylsiloxane, 0.025 g of di-tert-butylhydroxytoluene, 21.475 g of caprylic/capric triglycerides and 1.0 g of dimethicone/trimethyl siloxysilicate were placed in a tank equipped with a stirrer. The mixture was homogenized with vigorous stirring (1000 rpm). 0.5 g of capsules of Example H was then added. The mixture was homogenized again with vigorous stirring (1000 rpm). A liquid was thus obtained.

The composition applied to the body releases perfume during massaging and in the course of the day, on contact with perspiration or moisture.

Example 5: Massage Oil

Similarly, a massage oil having the following composition was prepared:

| Ingredients | (weight %) |
| --- | --- |
| Cyclopentadimethylsiloxane | 32 |
| Caprylic/capric triglycerides | 40.95 |
| Isopropyl palmitate | 22 |
| Perfume capsules of Example H | 1 |
| Dimethicone/trimethyl siloxysilicate | 2 |
| Di-tert-butyl-4-hydroxytoluene | 0.05 |
| Perfume | 2 |
| Total | 100.00 |

The perfume capsules of Example H may be replaced with the capsules of Examples A to G described previously.

The composition applied to the body releases perfume during massaging and in the course of the day, on contact with perspiration or moisture.

Example 6: Massage Oil

In a similar manner, a massage oil having the following composition was prepared:

| Ingredients | (weight %) |
| --- | --- |
| Cyclopentadimethylsiloxane | 32 |
| Caprylic/capric triglycerides | 40.95 |
| Isopropyl palmitate | 22 |
| Perfume capsules of Example A | 1 |
| Dimethicone/trimethyl siloxysilicate | 2 |
| Di-tert-butyl-4-hydroxytoluene | 0.05 |
| Perfume | 2 |
| Total | 100.00 |

The perfume capsules of Example A may be replaced with the capsules of Examples B to H described previously.

The composition applied to the body releases perfume in the course of the day, on contact with perspiration or moisture.

Example 7: Hair Oil

In a similar manner, a hair oil having the following composition was prepared:

| Ingredients | (weight %) |
| --- | --- |
| Sesame oil | 15.0 |
| Sweet almond oil | 12.1 |
| Isododecane | 14.3 |
| Ethylhexyl methoxycinnamate | 0.5 |
| Hydrogenated polyisobutene | 20.0 |
| Perfume | 3.0 |
| Isopropyl palmitate | 34.1 |
| Perfume capsule of Example A | 1.0 |

The perfume capsules of Example A may be replaced with the capsules of Examples B to H described previously.

After applying the composition to the hair, it is noted, when the individual perspires or on contact with sebum or moisture, that perfume is released in the course of the day.

The invention claimed is:

1. An anhydrous composition in oil form comprising:
   1) particles comprising a core containing at least one beneficial agent and an envelope surrounding the core; said envelope comprising at least one hydrophobically modified polysaccharide selected from the group consisting of starch ($C_5$-$C_{20}$) alkenyl succinates and at least one water-soluble carbohydrate selected from the group consisting of maltodextrins; said particles simultaneously having a poured powder density ranging from 300.0 g/l to 600.0 g/l and an absolute density of greater than 1.0; wherein the particles are spherical, have a number-mean diameter ranging from 1 to 30 μm and a volume-mean diameter ranging from 5 to 150 μm; and
   2) an oily phase, and
   wherein the particles comprising the at least one beneficial agent are obtained according to a process comprising the following steps:
   preparing an aqueous solution formed from a mixture of the at least one water-soluble carbohydrate and the at least one hydrophobically modified polysaccharide, adding the at least one beneficial agent, and stirring the whole so as to form an emulsion;
   homogenizing said emulsion at high pressure at a pressure ranging from 10 to 200 bar;
   spraying said emulsion in a drying chamber; and
   extracting the water for a time not exceeding 3 hours with a fluid under pressure so as to obtain particles comprising the at least one beneficial agent.

2. The composition as claimed in claim 1, further comprising a physiologically acceptable medium.

3. The composition as claimed in claim 1, in which the particles have a number-mean diameter ranging from 2 to 15 μm and a volume-mean diameter ranging from 10 to 100 μm.

4. The composition as claimed in claim 1, in which the at least one hydrophobically modified polysaccharide is sodium starch octenyl succinate.

5. The composition as claimed in claim 1, in which the at least one hydrophobically modified polysaccharide represents from 20% to 90% by weight, relative to the total weight of the envelope of the particle.

6. The composition as claimed in claim 1, in which the at least one water-soluble carbohydrate is selected from the group consisting of maltodextrins with a D.E. ranging from 4 to 20.

7. The composition as claimed in claim 1, in which the at least one water-soluble carbohydrate represents from 10% to 80% by weight relative to the total weight of the envelope of the particle.

8. The composition as claimed in claim 1 in which the envelope is formed from
   a) at least one starch ($C_5$-$C_{20}$)alkenyl succinate in an amount ranging from 20% to 90% by weight relative to the total weight of the envelope of the particle and
   b) at least one maltodextrin with a D.E. ranging from 4 to 20 in an amount ranging from 10% to 80% by weight relative to the total weight of the envelope of the particle.

9. The composition as claimed in claim 1, in which the at least one beneficial agent is selected from the group consisting of:
   (i) fatty substances;
   (ii) fragrancing substances;
   (iii) pharmaceutical active principles; and
   (iv) cosmetic active agents.

10. The composition as claimed in claim 1, in which the at least one beneficial agent is selected from the group consisting of fragrancing substances.

11. The composition as claimed in claim 1, in which the particles comprise at least one or more fragrancing substances with a saturating vapor pressure at 25° C. of greater than or equal to 10.0 Pa and said fragrancing substance(s) represent from 50% to 100% by weight relative to the total weight of the fragrancing substances present in the particles.

12. The composition as claimed in claim 1, wherein
   a) the particles comprise at least one fragrancing substance and
   b) the composition also comprises at least one fragrancing substance in free form, which may be identical to or different from the fragrancing substance present in said particles.

13. The composition as claimed in-claim 1, wherein any fragrancing substances that are present are exclusively encapsulated in the particles.

14. The composition as claimed in claim 1, further comprising at least one deodorant active agent and/or at least one antiperspirant active agent.

15. A consumer product, which is formed from comprises a composition as defined as claimed in claim 1.

16. A process for treating a human keratin material, which comprises applying to the surface of said human keratin material a composition as claimed in claim 1.

17. A cosmetic process for treating body odor and optionally human perspiration, which comprises applying to the surface of the keratin material a composition as claimed in claim 14.

* * * * *